United States Patent
Weiss et al.

(10) Patent No.: US 12,194,139 B2
(45) Date of Patent: Jan. 14, 2025

(54) METHOD FOR PREPARATION OF EFFERVESCENT GRANULES

(71) Applicant: Hermes Pharma GmbH, Pullach (DE)

(72) Inventors: Gerd Weiss, Munich (DE); Hans Höbart, Pullach (DE); Wolfgang Schiemenz, Pullach (DE)

(73) Assignee: Hermes Pharma GmbH, Pullach (DE)

( * ) Notice: Subject to any disclaimer, the term of this patent is extended or adjusted under 35 U.S.C. 154(b) by 0 days.

(21) Appl. No.: 18/254,286

(22) PCT Filed: Oct. 18, 2022

(86) PCT No.: PCT/EP2022/078921
§ 371 (c)(1),
(2) Date: May 24, 2023

(87) PCT Pub. No.: WO2023/066904
PCT Pub. Date: Apr. 27, 2023

(65) Prior Publication Data
US 2023/0381095 A1  Nov. 30, 2023

(30) Foreign Application Priority Data
Oct. 18, 2021  (EP) .................................. 21203232

(51) Int. Cl.
*A61K 9/46*  (2006.01)
*A61K 9/16*  (2006.01)

(52) U.S. Cl.
CPC .......... *A61K 9/0007* (2013.01); *A61K 9/1611* (2013.01); *A61K 9/1682* (2013.01)

(58) Field of Classification Search
None
See application file for complete search history.

(56) References Cited

U.S. PATENT DOCUMENTS

| | | |
|---|---|---|
| 4,867,942 A | 9/1989 | Gerhard et al. |
| 5,503,846 A * | 4/1996 | Wehling ............... A61K 9/0007 514/951 |
| 7,972,623 B2 | 7/2011 | Gergely et al. |

FOREIGN PATENT DOCUMENTS

WO    WO 94/21239    9/1994

OTHER PUBLICATIONS

"Handbook of Pharmaceutical Granulation Technology" In: "Handbook of Pharmaceutical Granulation Technology", Jan. 2, 2005 (Jan. 2, 2005), XP055435065, pp. 1-624.

* cited by examiner

*Primary Examiner* — Patricia Duffy
*Assistant Examiner* — Garen Gotfredson
(74) *Attorney, Agent, or Firm* — Hoxie & Associates LLC

(57) ABSTRACT

The invention provides a method for the preparation of effervescent granules wherein the reactive, effervescent components (one acidic and one alkaline $CO_2$-generating component) are brought to reaction with one another under stirring in a vacuum (100-900 mbar) in an evacuable mixing chamber, with said mixing chamber being evacuated to a first vacuum value $p_1$, and then 're-evacuated' to said first vacuum value $p_1$ again, optionally repeatedly, once the pressure has increased to a second vacuum value $p_2$ due to the progressing $CO_2$ formation of the effervescent reaction. The method is carried out in such a way that during at least the effervescent reaction step(s) the stirring speed in the mixing chamber exhibits a Froude number (Fr) of 0.5 or higher, preferably 0.8 or higher, more preferably 0.9 or higher; such as, in the range of 0.50 to 8.00, or 0.80 to 8.00, or 0.90 to 8.00.

20 Claims, 1 Drawing Sheet

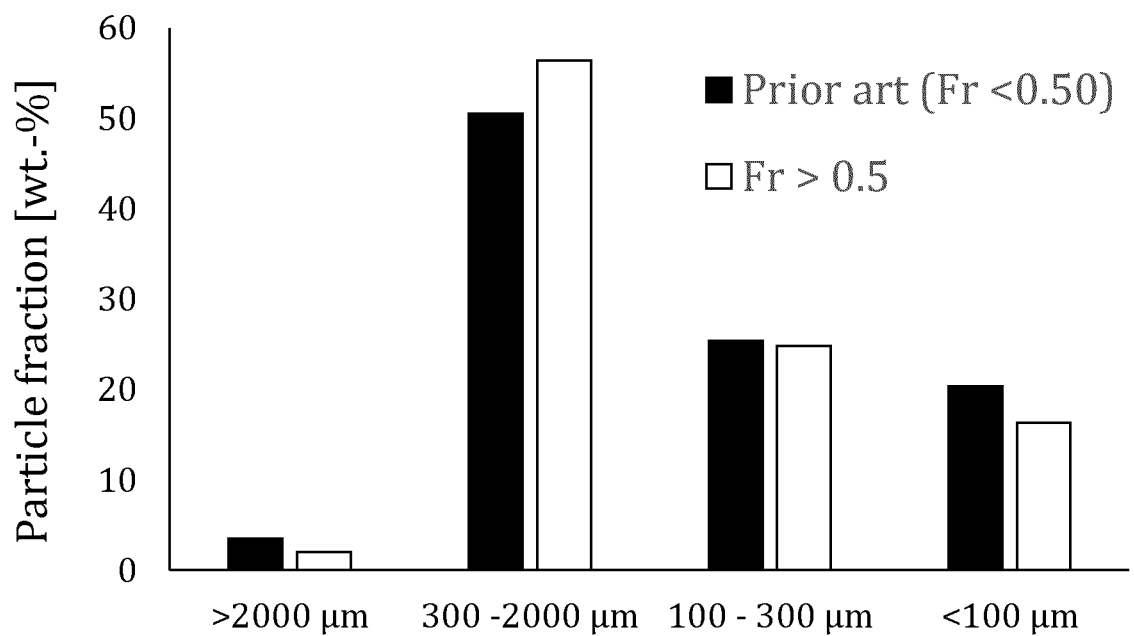

METHOD FOR PREPARATION OF EFFERVESCENT GRANULES

CROSS-REFERENCE TO RELATED APPLICATIONS

This application is a United States Application under 35 U.S.C. § 371 claiming priority to and the benefit of PCT Application No. PCT/EP2022/078921, filed on Oct. 18, 2022, which claims priority to European Patent Application No. 21203232.0, filed on Oct. 18, 2021, the contents of each of which are hereby incorporated by reference in their entireties.

BACKGROUND OF THE INVENTION

The invention relates to methods for preparing effervescent granules under vacuum in an evacuable mixing chamber (e.g., a horizontally oriented, evacuable mixing chamber), and in particular, methods using higher stirring speeds than previously considered suitable for the preparation of effervescent granules.

Effervescent granules can be prepared by mixing and granulating the two reactive components—at least one acidic (e.g., edible, organic acids) and at least one alkaline carbon dioxide ($CO_2$)-generating (e.g., carbonates or bicarbonates)—with one another. Optionally, polar liquids such as aqueous or hydro-alcoholic granulation liquids or binder solutions can be added for a so-called reactive granulation; i.e., the acidic and alkaline components start to react with one another upon addition of the polar liquids, thereby generating $CO_2$ and water. This nascent water generated by the effervescent reaction may then trigger, or sustain, a progressing effervescent reaction to an undesired extent. The preparation of effervescent granules, and in particular, said reactive granulation, thus requires a more careful and fine-tuned control of the humidity-levels in the powder bed of the reactive components than granulation processes for non-effervescent components. This applies in particular to effervescent granules which contain within said granules a pharmaceutically active ingredient (API), or drug, since effervescence-related weight losses of about 10% or higher and/or unreproducible losses would detrimentally affect the dosing accuracy for the resulting drug-laden effervescent granules.

The reactive granulation step can, for instance, be performed directly in an evacuable mixing chamber in which a vacuum is employed for drying; i.e., for removing both water that is introduced into the chamber as (part of) the granulation liquid or binder solution, and water that is co-generated along with $CO_2$ in the effervescent reaction. Examples of such prior art processes using vacuum as a drying means during the preparation of effervescent granules are described, for instance, in EP1656113B1. Therein, the authors describe a process performed in an evacuable container in which the vacuum is 'cycled', or oscillated, repeatedly between two vacuum values in the range of 200 to 900 mbar, with the effervescent reaction and the resulting $CO_2$-formation leading to continued pressure increase(s) from a first set value to a second set value. This so-called 'pendulum vacuum' is helping to keep the extent of the effervescent reaction during granulation under control. The process is stopped at the end by drying in the vacuum (e.g., after a set maximum number of cyclical repetitions, or a set maximum reaction time), and involves no intermittent drying.

In absence of an inlet-air-driven fluidized bed moving and drying the granules, stirring is required in the process of EP1656113B1 to facilitate both drying and even distribution of the added granulation liquid(s). EP1656113B1 is silent on specific stirring speeds; merely a maximum load for the stirring apparatus is discussed as an optional safety measure. It is known, though, that the processes described therein were performed in evacuable mixing devices such as the so-called TOPO granulator which allows maximum stirring speeds of about 20-25 rpm.

Faster stirring speeds were commonly advised against for the preparation of effervescent granules in order to keep the energies applied to the product bed low, and allow for a gentle, only minimally disturbed surface passivation of the effervescent granules (e.g., surface passivation of the highly hydrophilic citric acid crystals with citrate salts), and to thereby keep the effervescent reaction under control more effectively. Prior art such as WO9421239A1—which teaches faster stirring speeds in the preparation of effervescent granules—describe suboptimal yields such as below 85%, or even below 80%; the remainder of the granulated mass is lost due to poorly controlled effervescence. While yields of about 75-80% may appear good enough for drug-free effervescent granules, matters are far less favourable when preparing effervescent granules that comprise a drug substance. In the latter case, it becomes more important to keep material losses during the granulation process to a minimum and aim for yields of at least 90%, preferably 95%, not only from a cost-efficiency perspective but also from a dosing accuracy viewpoint.

However, at the same time, for a number of products and processes the slower stirring speed used in prior art processes (such as described in EP1656113B1, or as limited by the maximum stirring speeds provided by the device used) can be suboptimal; for instance, in terms of homogenously distributing active ingredients and/or granulation liquids in the excipients blend, and/or in cases where the effervescent reaction is not as easily initiated (e.g., when working with calcium- and/or magnesium carbonates as the $CO_2$-generating component).

Moreover, slower maximum stirring speeds, such as up to about 20-25 rpm, also result in less heat transfer within the product bed (leading to longer and often less manageable processing times), as well as fewer options to deliberately influence product parameters, such as the granules' particle size and/or density, by varying the stirring speed.

It is thus an object of the present invention to provide methods for preparing effervescent granules under vacuum in an evacuable mixing chamber, in particular, methods using higher stirring speeds than previously considered suitable for the preparation of effervescent granules. Further objects of the invention will be clear on the basis of the following description of the invention, examples and claims.

SUMMARY OF THE INVENTION

In a first aspect, the invention relates to a method for the preparation of effervescent granules, wherein at least one acidic effervescent component and at least one alkaline $CO_2$-generating effervescent component as the reactive components are brought to reaction with one another under stirring in a vacuum in an evacuable mixing chamber, wherein, after loading at least the reactive components, the mixing chamber is evacuated to a first vacuum value $p_1$, and wherein the mixing chamber is evacuated to said first vacuum value $p_1$ again, optionally repeatedly, once the pressure has increased to a second vacuum value $p_2$ as a result of the progressing $CO_2$-formation of the effervescent reaction in the mixing chamber, and wherein the effervescent reaction is carried out in a vacuum range $p_1$ to $p_2$ of 100 to 900 mbar, and wherein the effervescent reaction is stopped by drying the effervescent granules under vacuum in a 'stop'-drying step, wherein during at least the effervescent reaction step(s) the stirring speed in the mixing chamber exhibits a Froude number (Fr) in the range of 0.50 to 8.00, preferably in the range of 0.80 to 8.00, more preferably in the range of 0.90 to 8.00.

In a second aspect, the present invention provides effervescent granules obtained by the method according to the first aspect of the invention.

DESCRIPTION OF THE FIGURES

FIG. 1 depicts the results of a sieve analysis, and its resulting particle size fractions in wt.-%, for the Mg containing effervescent granules as obtained from Example 1A versus those obtained with a prior art process run in a lab-scale TOPO-device and using low stirring speeds of about Fr 0.06 to 0.25 during the effervescent reaction steps

DETAILED DESCRIPTION OF THE INVENTION

In a first aspect, the invention relates to a method for the preparation of effervescent granules, wherein at least one acidic effervescent component and at least one alkaline $CO_2$-generating effervescent component as the reactive components are brought to reaction with one another under stirring in a vacuum in an evacuable mixing chamber, wherein, after loading at least the reactive components, the mixing chamber is evacuated to a first vacuum value $p_1$, and wherein the mixing chamber is evacuated to said first vacuum value $p_1$ again, optionally repeatedly, once the pressure has increased to a second vacuum value $p_2$ as a result of the progressing $CO_2$-formation of the effervescent reaction in the mixing chamber, and wherein the effervescent reaction is carried out in a vacuum range $p_1$ to $p_2$ of 100 to 900 mbar, and wherein the effervescent reaction is stopped by drying the effervescent granules under vacuum in a 'stop'-drying step, wherein during at least the effervescent reaction step(s) the stirring speed in the mixing chamber exhibits a Froude number (Fr) in the range of 0.50 to 8.00, preferably in the range of 0.80 to 8.00, more preferably in the range of 0.90 to 8.00.

The term 'effervescent reaction step' as used herein refers to the parts of the preparation method in which the actual effervescent reaction takes place, i.e., in which at least the reactive components in the evacuable mixing chamber are in contact with a granulating liquid and thus in an effervescent reaction with one another, while stirring is employed to distribute, or spread, at least the liquids (both the added granulating liquid and the nascent water stemming from the effervescent reaction) throughout the product-bed. This applies irrespective of the order in which the reactive components and the granulating liquid are combined; e.g., whether the granulating liquid is added to a dry blend of both reactive components, or whether the granulating liquid is initially added to only one of the two reactive components (e.g., only to the acid(s) first), with the other, or missing, reactive component (e.g., the alkaline component(s)) then being added to the pre-wetted blend. Either way, the resulting effervescent granules may then be dried in a subsequent 'stop'-drying step that is understood to be separate from the 'effervescent reaction step' insofar as it interrupts, or stops, the effervescent reaction taking place inside the mixing chamber.

The term 'effervescent reaction step(s)' (plural) refers to the case where, within the preparation of one batch, there may be repetitions of effervescent reaction steps, optionally with intermediate 'stop'-drying step(s) in between.

The term 'vacuum', as used herein, refers to reduced pressures compared to the ambient pressure present, or atmospheric pressure, at a given location (i.e., typically about 1 bar), and more specifically to reduced pressures in the range of 0.01 mbar to 900 mbar. In other words, even the higher second vacuum value $p_2$ will be lower than the prevailing atmospheric pressure, typically by at least 10%.

Regarding the mixing chamber being evacuated to the first vacuum value $p_1$ after loading at least the reactive components into it, and then re-evacuated to $p_1$, optionally repeatedly, once the pressure has increased to the second vacuum value $p_2$ due to the progressing $CO_2$-formation of the effervescent reaction in the mixing chamber, it should be understood that this kind of vacuum control is used at least during the actual effervescent reaction step(s), and is responsible for a more controlled effervescent reaction, thereby leading to higher yields. In other words, in one embodiment of the preparation method according to the first aspect, the mixing chamber is evacuated to a first vacuum value $p_1$ at the beginning of the effervescent reaction step(s), and then evacuated to said first vacuum value $p_1$ again, optionally repeatedly, once the pressure has increased to a second vacuum value $p_2$ as a result of the progressing $CO_2$-formation of the effervescent reaction in the mixing chamber.

While optionally this kind of vacuum control is also used during the 'stop'-drying step(s), or any subsequent further processing steps herein, the present invention does not refer to preparation processes where the effervescent reaction step(s) are performed at ambient pressure and vacuum is only employed later in the process; for instance, to facilitate subsequent drying steps.

The Froude number 'Fr' as used herein refers to a dimensionless number aimed at describing the movement and fluid mechanics of flowable solids, such as granules or pellets, under stirring, more specifically under stirring predominantly in horizontal mixing devices (i.e., devices wherein the orientation of the central longitudinal axis of the mixing chamber and the stirrer moving therein is oriented horizontally). The movement behavior of flowable particles in horizontal mixing devices depends on a variety of factors, such as the speed and geometry of the stirring tool(s), the product properties, and the degree of filling of the mixing chamber, or drum. While, strictly speaking, the flowable particles have their own Froude number defining their movement behavior, it is more common, for the sake of simplicity, to provide the Froude number of the stirring tool to characterize the movement behavior.

Hence, the Froude number, as used herein, relates to the stirring tool and is calculated according to the following formula:

Froude number $Fr = R\omega^2/g$ with R=drum, or mixing chamber radius [m];
g=gravitational acceleration=9.81 m/s$^2$; and
$\omega$=angular velocity=$2\pi \cdot n$ (with n=rotational speed [s$^{-1}$]).

In other words, the Froude number Fr describes a ratio of the centrifugal acceleration of the stirring tool's outer ends $R\omega^2$ (assuming the radius of the stirring tool to be similar to the drum radius, or mixing chamber radius) to the gravitational acceleration g.

The benefit of Froude numbers is that they allow for a better comparability between different mixing devices. When operating two mixing devices of different geometries at the same Froude number, this will typically result in the same, or at least similar, particle bed movements; the same would not be true, though, when operating the two at the same rotations-per-minute (rpm).

As mentioned above, the Froude number is aimed predominantly at the movement and fluid mechanics of flowable solids under stirring in horizontal mixing devices. Thus, in one of the preferred embodiments of the invention, the method of the first aspect of the invention is carried out in a horizontal mixing device; or, in other words, the evacuable mixing chamber employed in the preparation method according to the first aspect of the invention, namely its central longitudinal axis, is oriented horizontally. This also means that the stirring device, or stirrer, namely the central axis thereof, is oriented horizontally, with the stirrer's central axis typically coinciding with the central longitudinal axis of the evacuable mixing chamber. In a specific embodiment, the evacuable mixing chamber is oriented horizontally throughout the complete preparation process of the effervescent granules as outlined above; i.e., the device does not tilt, for instance, during the preparation process. Depending on where the product outlet opening of the mixing chamber is positioned, the latter embodiment shall not exclude the possibility, though, that the device, or more specifically the evacuable mixing chamber thereof, may be tilted, or moved out of its horizontal orientation, once the preparation process is finished and the dried effervescent granules need to be emptied from the device and into storage containers.

According to the method of the first aspect of the invention, the mixing chamber is evacuated to a first vacuum value $p_1$, and 're-evacuated' to said first vacuum value $p_1$ again, optionally repeatedly, once the pressure has increased to a second vacuum value $p_2$ as a result of the progressing $CO_2$-formation of the effervescent reaction in the mixing chamber. In other words, the effervescent reaction inside the evacuable mixing chamber is taking place in repeating cycles, with one complete 'cycle' (or 1.00 cycle) being defined as one pressure increase from $p_1$ to $p_2$, and from $p_2$ back to $p_1$. It should be understood, though, that depending on the desired extent of the effervescent reaction taking place inside the evacuable mixing chamber upon addition of aqueous liquids, the method may involve incomplete cycles, such as 0.80 cycles, 1.50 cycles or 3.30 cycles. The number of cycles is, of course, interconnected with the vacuum values chosen; for instance, the lower the first vacuum value $p_1$, the more water is removed from the reaction upon decreasing the pressure from second ($p_2$) to first vacuum value ($p_1$), and the slower the effervescent reaction when restarting from $p_1$. Vice versa, the higher second vacuum value $p_2$, the faster the effervescent reaction can become. Thus, by choosing the vacuum value $p_1$ and $p_2$, the extent of the effervescent reaction (i.e., how much of the effervescent mixture is already reacted to $H_2O$ and $CO_2$ during the granulation process) can be controlled.

Furthermore, according to the method of the first aspect of the invention, the stirring speed in the mixing chamber exhibits a Froude number (Fr) in the range of 0.50 to 8.00 during at least the effervescent reaction step(s), preferably in the range of 0.80 to 8.00, more preferably in the range of 0.90 to 8.00. These stirring speeds are higher than previously considered suitable for the preparation of effervescent granules. For instance, during standard prior art processes performed in a TOPO-600 vacuum granulator, the maximum stirring speed of 20 rpm of said device correspond to a Froude number of only 0.25.

In a further embodiment, the stirring speed in the mixing chamber exhibits a Froude number (Fr) of 0.25 or higher during the 'stop'-drying step(s). For instance, in a specific embodiment, the stirring speed in the mixing chamber exhibits a Froude number (Fr) of 0.25 to 5.00 during the 'stop'-drying step(s). The term 'stop'-drying step, as used herein, refers to any drying step that interrupts, or stops, the effervescent reaction taking place inside the evacuable mixing chamber, or aims at such an interruption or stop, irrespective of whether this 'stop'-drying step is an intermediate step, or a final step, of the method according to the first aspect of the invention. In other words, this method also encompasses embodiments which involve intermediate 'stop'-drying steps aimed at temporarily interrupting, or 'pausing', the effervescent reaction 'mid-process'.

Typically, the 'stop'-drying step(s) involve heating of the product inside the mixing chamber beyond room-temperature (e.g., by heating the jacketed mixing chamber), with the vacuum optionally being switched off, at least intermittently, to allow for improved, faster heat transfer. It should further be understood that the terms 'stop'-drying step and drying step are not necessarily synonymous herein, since not every drying step is performed in order to stop the effervescent reaction. For instance, after a last 'stop'-drying step, the already dried effervescent granules might be processed further, such as by mixing them with one or more pharmaceutically or nutraceutically acceptable active ingredients and/or excipients. This may then introduce into this mixture residual moisture, or even solvents, that need to be dried out of the resulting final mixture in a drying step which does not interrupt, or stop, effervescence in the already dried effervescent granules anymore.

For intermediate 'stop'-drying steps (i.e., when the effervescent granules get moistened again thereafter, and/or the effervescent reaction gets restarted otherwise), the stirring speed can be chosen in a range of Fr 0.25 to 5.00. In the last 'stop'-drying step (and any steps subsequent thereto, such as mixing the dried granules with further ingredients like aroma, sugars or the like), the stirring speed is typically chosen to be lower, e.g., Froude numbers in the range of 0.25 to 4.30, or 0.25 to 3.80, or 0.25 to 2.00, or 0.25 to 1.60, or 0.25 to 1.10, to make sure that excessive abrasion and/or comminution of the dried effervescent granules is avoided, thus, resulting in a more stable surface passivation of the effervescent granules, as well as shortened drying times since the effervescent reaction has less chances of restarting over and over again on comminution-induced fracture surfaces of the effervescent granules.

In one embodiment, the stirring speed in the mixing chamber is higher during at least the effervescent reaction step(s) than during the 'stop'-drying step(s).

In one embodiment, the effervescent reaction is carried out in a vacuum range $p_1$ to $p_2$ of 150 to 850 mbar. In a further embodiment, the difference between $p_1$ and $p_2$, at least during the effervescent reaction step, is in the range of from 200 to 500 mbar, or from 250 to 450 mbar, or from 300 to 400 mbar. In a specific embodiment, the effervescent reaction is carried out in a vacuum range $p_1$ to $p_2$ of 150 to 450 mbar, or in a vacuum range $p_1$ to $p_2$ of 450 to 850 mbar. Typically, the lower the vacuum, the more easily controllable, or stoppable, the effervescent reaction. This is useful, for instance, when working with sodium- or potassium carbonates, or when working with smaller-sized raw-material grades of the effervescent components (e.g., powders vs.

granules). Furthermore, the inventors found that effervescent granules prepared at the lower vacuum ranges, such as $p_1$ and $p_2$ staying at ≤450 mbar, are particularly suited for effervescent compositions comprising drugs that are sensitive to hydrolysis, oxidation, acids, bases including carbonates, alkali-ions and/or earth-alkali ions (e.g., cimetidine, captopril, or beta-carotene).

In one embodiment, the at least one acidic effervescent component is an organic acid or a mixture of organic acids, preferably an organic acid selected from the group consisting of citric acid, tartaric acid, malic acid, fumaric acid, adipic acid, or a mixture thereof. In a specific embodiment, the at least one acidic effervescent component comprises, or consists of, citric acid.

In one embodiment, the at least one alkaline $CO_2$-generating effervescent component selected from the group consisting of hydrogen carbonates and carbonates of alkaline metals and alkaline earth metals, or a mixture thereof, preferably selected from the group consisting of sodium hydrogen carbonate, sodium carbonate, potassium hydrogen carbonate, potassium carbonate, magnesium carbonate, and calcium carbonate, or a mixture thereof.

In one embodiment, the first effervescent reaction step is preceded by a prewarming step for bringing at least one, optionally all, of the reactive components to a target product temperature prior to reacting them with one another. In a specific embodiment, the stirring speed in the mixing chamber exhibits a Froude number (Fr) in the range of 0.50 to 8.00 during the prewarming step(s) and the effervescent reaction step(s), preferably in the range of 0.80 to 8.00, more preferably in the range of 0.90 to 8.00. In a further specific embodiment, the at least one acidic effervescent component comprises, or consists of, citric acid, and at least the citric acid is brought to a target product temperature, for instance about 55-70° C., or 55-65° C., prior to reacting it with the at least one alkaline $CO_2$-generating effervescent component.

In one embodiment, the effervescent reaction is initiated by addition of a granulating liquid, optionally an aqueous, alcoholic or hydroalcoholic granulating liquid. The effervescent reaction then proceeds under stirring while the liquids (both the added granulating liquid and the nascent water stemming from the effervescent reaction itself) are spread, or distributed, across the product bed, thereby forming moist effervescent granules. In a specific embodiment, said granulating liquid is added in two or more fractions thereof, with an intermediate 'stop'-drying step in between the additions of the two or more fractions.

Alternatively, or in addition thereto, two or more different granulating liquids may be used (differing in either quality and/or quantity of its components), with an intermediate 'stop'-drying step in between the additions of the different granulating liquids. For instance, the granulating liquid added first may be used to help initiate the effervescent reaction (optionally, an acidic granulating liquid), and a second granulating liquid, comprising e.g., a polymeric binder, may be added to improve the compressibility of the effervescent granules.

The granulating liquid may, for instance, be introduced into the evacuable mixing chamber via at least one top-spray nozzle; this approach typically allows for smaller droplets and thus a more even distribution of the granulating liquid across the product bed of the flowable particle compared to devices aspiring the granulating liquid into the mixing chamber via an inlet port using the vacuum inside the mixing chamber. The more even distribution of granulating liquid helps to control the effervescent reaction inside the evacuable mixing chamber and by preventing the formation of reactive 'wet nests'.

In one embodiment, the effervescent granules obtained in the 'stop'-drying step, more specifically the last 'stop'-drying step, are processed further in the same evacuable mixing chamber, and the stirring speed in the mixing chamber exhibits a Froude number (Fr) of 0.25 or higher during this at least one further processing step. In a specific embodiment, the effervescent granules obtained in the 'stop'-drying step, more specifically the last 'stop'-drying step, are processed further in the same evacuable mixing chamber by mixing them with one or more additional components selected from pharmaceutically or nutraceutically acceptable active ingredients and/or pharma-ceutically or nutraceutically acceptable excipients. As mentioned above, the mixing speed is typically chosen to be in the range of Fr 0.25 to 4.30, or 0.25 to 3.80, or 0.25 to 2.00, or 0.25 to 1.60, or 0.25 to 1.10 during the at least one further processing step, to make sure that excessive abrasion and/or comminution of the dried effervescent granules is avoided.

The mixing step can occur both by a dry mixing step (e.g., adding further dry powders and/or granules to the effervescent granules obtained in the 'stop'-drying step), more specifically the last 'stop'-drying step; and/or by a wet mixing step, such as spraying the effervescent granules with an aqueous, alcoholic or hydroalcoholic coating comprising the additional component(s).

Optionally, the pharmaceutically or nutraceutically acceptable active ingredients is selected from analgesic drugs, including e.g., non-steroidal anti-inflammatory drugs (NSAIDs), expectorant drugs, diuretic drugs, bisphosphonate drugs, captopril, vitamins including e.g., cholecalciferol, minerals including e.g., magnesium, calcium, or iron, and/or herbal extracts. Further optionally, the pharmaceutically or nutraceutically acceptable excipient is selected from sugars, sugar alcohols, sweeteners, aromas, binders, diluents, anti foaming agents, lubricants, colourants, and/or stabilizers for the effervescent granules (e.g., mono-sodium citrate as an 'effervescent-reaction stopper', or (further) sodium carbonate as a drying agent). In other words, these excipients may be added to aid properties such as stability, taste, organoleptic appearance, and/or compactability of the effervescent granules.

In one embodiment, the effervescent granules prepared by the method according to the invention exhibit a loss-on-drying of ≤1.50 wt.-%, based on the initial weight prior to drying, preferably ≤1.00 wt.-%, more preferably ≤0.75 wt.-%, and further preferably ≤0.50 wt.-%, as determined gravimetrically after 15 minutes at 70° C. and ambient pressure (e.g., using a halogen moisture analyzer like HC103 by Mettler). For the more reactive effervescent couples, such as those based on sodium- and/or potassium carbonates, the LOD should preferably be ≤0.50 wt.-%.

In one embodiment, the effervescent granules prepared by the method according to the invention exhibit a Hausner ratio (i.e., tapped bulk density divided by freely settled bulk density) in the range of 1.10 to 1.40, or 1.15 to 1.30.

In one embodiment, the effervescent granules prepared by the method according to the invention are storage stable, which means there is no gas formation observed in an air tight closed container (e.g., an aluminium-lined sachet) filled with either said granules, or tablets prepared therefrom, even if stored at temperatures up to 55° C. for at least 48 hours and up to 7 days.

In one embodiment, the effervescent granules prepared by the method according to the invention, when compressed into effervescent tablets of a hardness in the range of 60 to 120 N, exhibit dissolution times in 100 to 250 mL water at room temperature (20±5° C.) of 150 seconds, preferably 120 seconds, more preferably 90 seconds, and further preferably ≤60 seconds.

In one of the preferred embodiments of the method according to the invention, the evacuable mixing chamber is temperature-controlled, i.e., it can be both heated or cooled; for instance, using a jacketed mixing chamber.

In a second aspect, the present invention provides effervescent granules obtained by the method according to the first aspect of the invention. Accordingly, any embodiments, or specific or preferred embodiments, disclosed herein in connection with the method according to the first aspect of the invention, may be applied to the resulting effervescent granules according to this second aspect of the invention.

The following examples serve to illustrate the invention, however should not to be understood as restricting the scope of the invention.

EXAMPLES

Example 1A—Effervescent Granules Containing Magnesium/Labscale (~7-8 kg)

For the preparation of multiple batches of magnesium (Mg)-containing effervescent granules, about 3.29 kg citric acid was loaded into the evacuable mixing chamber of a ploughshare mixing device (here, a 20 L mixing drum of a Lödige laboratory mixing device, more specifically a horizontal mixing drum; Gebrüder Lödige Maschinenbau GmbH; Germany), and heated under stirring to about 65° C. for about 10-14 min, with the stirring speed exhibiting a Froude number (Fr) of 4.22-4.76 (equals about 160-170 rpm for the dimensions of said 20 L mixing drum). The jacket temperature was set at 70° C.

Thereafter, the citric acid is moistened over the course of about 2.5 minutes with about 14.5 mL water via the device's inlet port, while stirring at the highest stirring speed of the mixing device used (Fr 7.97; about 220 rpm), preferably using the chopper blades of the device during at least the first minute to avoid the formation, or presence, of larger agglomerates in the mixture.

Subsequently, about 0.51 kg magnesium oxide (MgO) and about 0.12 kg sodium bicarbonate ($NaHCO_3$) are added to the same mixing chamber, and granulated with the moistened citric acid under vacuum (about 15 mbar) for about 7 minutes at a temperature of 65-67° C., while stirring at a speed of about Fr 2.37-4.76 (about 120-170 rpm).

In the next step, the mixture is granulated further by adding about 86 mL of an ethanolic solution of citric acid (10% citric acid in 30% V/V ethanol) to the mixing chamber via the device's inlet port over the course of about 4-5 minutes total. During the first 1-2 minutes, the stirring speed ranges from about Fr 4.76-7.97 (about 170-220 rpm), and, optionally, the chopper blades are used. For the remaining 3 minutes the chopper blades, if used before, are switched off and the stirring speed slightly reduced to about Fr 3.71-4.76 (about 150-170 rpm). Due to the exothermic reaction, the temperature in the mixing chamber may rise to about 70-72° C.

Subsequently, about 1.01 kg magnesium carbonate ($MgCO_3$), about 1.24 kg citric acid, about 0.35 kg sodium bicarbonate ($NaHCO_3$) and about 0.38 kg potassium bicarbonate ($KHCO_3$) are added to the mixing chamber, and granulated at a temperature of about 62-67° C., a stirring speed of 1.05-4.22 (about 80-160 rpm), and using a vacuum that is cycling from $p_1$=450 mbar to $p_2$=850 mbar (due to the ongoing effervescent reaction in the evacuable mixing chamber), for a total of about 3.5-5 minutes. This typically equals about 0.8-1.5 cycles for this product.

For the batches tested, it was surprisingly observed that the stirring speeds during these granulation steps (i.e., before drying and when the effervescent granules are still moist) appear to have an impact on the density of the resulting granules. For instance, it was found that stirring at slower stirring speed during at least one of the granulation steps yielded lower densities of the effervescent granules, than higher stirring (e.g., in this example Fr 1.05≈80 rpm: 0.61 g/mL versus Fr 4.22≈160 rpm: 0.91 g/mL). Without wishing to be bound by theory, it is believed that this effect is the result of the effervescent granules still being moist and thus potentially more pliable prior to drying them, so that a faster stirring speed may result in compacting them. This effect can be used to deliberately influence the properties of the resulting effervescent granules by selecting faster stirring speeds in at least one, or all, of the granulation steps if more compact effervescent granules are desired.

In the next step, the mixture is again granulated further by adding about 230 mL of an aqueous citric acid solution (50%) to the mixing chamber via the device's inlet port using a vacuum that is cycling from $p_1$=450 mbar to $p_2$=850 mbar (due to the ongoing effervescent reaction in the evacuable mixing chamber), over the course of about 5-8 minutes total (equals about 4-5 cycles). During the first 2-3 minutes, the stirring speed is about Fr 6.59 (about 200 rpm), and, optionally, the chopper blades are used. For the remaining time, the chopper, if used before, are switched off and the stirring speed slightly reduced to about Fr 1.05-4.22 (about 80-160 rpm).

Thereafter, the product is dried, in an initial 'stop'-drying step, at a temperature of about 58-60° C., and a stirring speed of Fr 1.05-4.76 (about 80-170 rpm) while gradually reducing the pressure to about 30 mbar. Surprisingly, for the batches tested, it was observed by the inventors that the stirring during this initial 'stop'-drying step appears to have an impact on both the drying time and the density of the resulting granules. The initial 'stop'-drying step can thus be used to influence the properties of the resulting effervescent granules by choosing both suitable stirring speeds and stirring durations during this step. For instance, it was found that interrupted stirring (or interval-stirring; IS) at slower stirring speeds, such as Fr 1.05 or 4.22, during the initial 'stop'-drying step actually decreased the total drying time and increased the yield compared to e.g., an uninterrupted stirring at Fr 4.76. This is contrary to the expectation that faster and/or consistent stirring would help to dry the effervescent granules quicker (due to e.g., an increased contact, and thus heat-exchange, of the moving granules bed with the heated parts/walls of the mixing chamber). Without wishing to be bound by theory, it is believed that this unexpected finding is the result of the granules surfaces being subject to stronger abrasion with high, consistent stirring, and in turn restarting the $CO_2$ and $H_2O$-forming effervescent reaction over and over again; i.e., in other words, the effervescent granule bed keeps 're-moistening' itself and dries slower.

It was furthermore found that both lower stirring rates (e.g., Fr 1-05 vs. Fr 4.76) as well as opting for interval-stirring (IS; i.e., stirrer switched off and on in intervals) are better suited to create effervescent granules with a lower bulk-density, as shown in Table 1 for the four exemplary lab-scale batches of Example 1A below:

TABLE 1

Effects of stirring speed and stirring duration during initial drying

| Stirring | | Yield [wt.-%] | Time till 15 mbar [min] | Bulk density [g/mL] |
|---|---|---|---|---|
| Speed (Fr) | Interval Stirring off/on [min] | | | |
| 4.76 | continuously on until 15 mbar | 92.5 | 68 | 0.91 |
| 4.22 | continuously on until 90 mbar; then 2/0.25 until 30 mbar | 94.5 | 60 | 0.79 |
| 4.22 | continuously on until 130 mbar; then 5.5/0.25 until 30 mbar | 95.0 | 55 | 0.71 |
| 1.05 | continuously on until 130 mbar; then 5.5/0.25 until 30 mbar | 95.0 | 52 | 0.61 |

After this initial 'stop'-drying step (pressure reduced to about 30 mbar), when the granules are not quite as sensitive anymore, the product is dried yet further, in a final 'stop'-drying step of about 15 min, using interval-stirring (5.5 min off/0.25 min on) at a stirring speed of Fr 4.22-4.76, with the heater optionally being switched off, reducing the pressure to mbar or below.

Optionally, aroma, sweeteners, dyes, as well as other excipients commonly used for adjusting the organoleptic and/or handling properties of effervescent granules (e.g., antifoaming agents, wetting agents, binders, etc), can then be added to the thus dried granular product Upon such additions, the stirring speed should preferably not be increased beyond the stirring speed of the final 'stop'-drying step to make sure that excessive abrasion and/or comminution of the dried effervescent granules is avoided.

The process yielded Mg-containing effervescent granules with a bulk density in the range of from 0.61 g/mL to 0.91 g/mL, a Hausner ratio in the range of from 1.32 to 1.37, and a median particle size (D50; as measured by dynamic image analysis, e.g., using a Camsizer® XT device) in the range of from about 260 μm to about 330 μm. The process yield was about 92-95 wt.-% based on the weights of the raw materials used. The effervescent granules of all tested lab-scale batches could be compressed into the target effervescent tablets with a weight of about 4.75 g, a hardness of about 90 N, and dissolution times of about 100±20 seconds in a glass of water (— 250 mL).

Moreover, the inventors observed that, advantageously, the effervescent Mg-containing granules prepared as described above inherently (i.e., without passing the granules through the device's outlet sieve first) contained less coarse granules and less fine powder compared to effervescent granules prepared with prior art processes stirred at lower Froude numbers of <0.5 during at least the effervescent reaction step (s). This can be seen, for instance, in FIG. 1 which depicts the results of a sieve analysis, and its resulting particle size fractions in wt.-%, for the Mg-containing effervescent granules of this example versus those obtained with a prior art process run in a lab-scale TOPO-device and using low stirring speeds of about Fr 0.06 to 0.25 during the effervescent reaction steps (yet lower during drying). In this sieve analysis, the terms 'coarse granules' and 'fine powder' refer to particles >2000 μm and <100 μm, respectively.

Effervescent granules containing lower amounts of fine powder and coarse granules are beneficial since this indicates a narrower particle size distribution, and furthermore may result in improved dosing accuracy, e.g., when said granules are compressed into effervescent tablets.

Example 1B—Effervescent Granules Containing Magnesium/Production Scale (≥500 kg)

Multiple batches of magnesium (Mg)-containing effervescent granules were prepared the same way as in Example 1A (i.e., same components, same order of steps) but using a larger, production scale mixing device equipped with an evacuable mixing chamber as well as a top-spray nozzle as the inlet port for granulation liquids (here, a 1600 L mixing drum of a Lödige VT1600 mixing device; also, a horizontal mixing device, or a mixing device with a horizontally oriented evacuable mixing chamber and stirrer; Gebrüder Lödige Maschinenbau GmbH; Germany), and adjusted stirring speeds as needed.

The stirring speeds in this specific production scale device are as follows:

| | | |
|---|---|---|
| Fr 0.25 ≈ 20 rpm | Fr 0.56 ≈ 30 rpm | Fr 0.99 ≈ 40 rpm |
| Fr 1.55 ≈ 50 rpm | Fr 2.23 ≈ 60 rpm | Fr 2.26 ≈ 65 rpm |
| Fr 3.49 ≈ 70 rpm | Fr 3.97 ≈ 80 rpm | Fr 6.2 ≈ 100 rpm |

The operation conditions for Examples 1A and 1B are described in Table 2 below.

TABLE 2

Processing conditions and granulate parameters Examples 1A and 1B

| Step | Lab scale | Production scale |
|---|---|---|
| Step 1 | 15 mbar | 15 mbar |
| Load citric acid; | 10-14 min: Fr 4.22-4.76 | 9-16 min: Fr 2.23 |
| Pre-heating | 55-65° C. | 55-65° C. |
| Step 2 | 15 mbar | 15 mbar |
| Moisten with $H_2O$ | 1 min: Fr 7.97 + chopper ~14.5 mL | 2 min: Fr 6.2 + chopper ~1 L |
| | 1.5 min: Fr 7.97 | 3 min: Fr 2.23 |
| Step 3 | 15 mbar | 15 mbar |
| Adding MgO and $NaHCO_3$; Granulate | 7 min: Fr 2.37-4.76 65-67° C. | 7 min: Fr 1.55-2.26 65-75° C. |

TABLE 2-continued

Processing conditions and granulate parameters Examples 1A and 1B

| | Lab scale | Production scale |
|---|---|---|
| Step 4<br>Adding ethanolic<br>citric acid solution;<br>Granulate further | 15 mbar<br>1-2 min: Fr 4.76-7.97 +<br>chopper ~86 mL<br>3 min: Fr 3.71-4.76<br>70-72° C. | 15 mbar<br>2.5-5 min: Fr 6.2 +<br>chopper ~6 L<br>3 min: Fr. 2.23-3.97<br>90-98° C. |
| Step 5<br>Adding $MgCO_3$,<br>citric acid and<br>$KHCO_3$;<br>Granulate further | $p_1$-$p_2$: 450-850 mbar<br>62-67° C.<br>3.5-5 min: Fr 1.05-4.22<br>0.8-1.5 cycles | $p_1$-$p_2$: 450-850 mbar<br>68-75° C.<br>2.5-5 min: Fr 0.99-3.49<br>1-2 cycles |
| Step 6<br>Adding aqueous<br>citric acid solution;<br>Granulate further | $p_1$-$p_2$: 450-850 mbar<br>2-3 min: Fr 6.59 +<br>chopper ~320 mL<br>3-5 min: Fr 1.05-4.22<br>4-5 cycles | $p_1$-$p_2$: 450-850 mbar<br>4-11 min: Fr 6.2 +<br>chopper ~13-16 L<br>5.5-8 min: Fr 0.56-3.49<br>2.3-4 cycles |
| Step 7<br>Initial 'stop'-drying | Fr 1.05-4.76 down to<br>90-130 mbar<br>then Fr 1.05-4.76 down to<br>30 mbar;<br>preferably with interval stirring<br>(e.g., 5.5 min off/0.25 min on)<br>58-60° C. | Fr 0.25 down to 130 mbar<br>then Fr 0.25 down to 25 mbar,<br>all with interval stirring<br>(5 min off/0.2 min on)<br>60-64° C. |
| Step 8<br>Final 'stop'-drying | 15 min: Fr 4.22-4.76<br>to 15 mbar or below;<br>preferably with interval stirring<br>(e.g., 5.5 min off/0.25 min on)<br>heater off | 15 min: Fr 0.25<br>to 15 mbar or below;<br>all with interval stirring<br>(5 min off/0.2 min on)<br>heater off |
| Step 9 (optional)<br>Adding aroma;<br>Blending<br>Parameters | — | Aroma added and blended in<br>5 min: Fr 0.25 |
| Yield | 92.5-95 wt.-% | 92-95 wt.-% |
| Bulk density | 0.61-0.91 g/mL | 0.62-0.77 g/mL |
| Hausner ratio | 1.22-1.36 | 1.28-1.30 |
| Loss-on-drying<br>(15 min/70° C./<br>ambient pressure) | 0.53-1.22 wt.-% | 1.13-1.42 wt.-% |
| D50 [μm] | 263.4-323.9 | 136.0-226.7 |

Example 2—Effervescent Granules Containing Potassium/Labscale (Here ~7-8 kg)

For the preparation of multiple batches of potassium (K)-containing effervescent granules, about 4.25 kg citric acid was loaded into the evacuable mixing chamber of a ploughshare mixing device (here, a 20 L mixing drum of a Lödige laboratory mixing device; Gebrüder Lödige Maschinenbau GmbH; Germany), and heated under stirring to about 55-65° C. (e.g., about 60° C.) for 6-11 min and applying a vacuum of about 15 mbar, with the stirring speed exhibiting a Froude number (Fr) of 1.33 (equals about 90 rpm for the dimensions of said 20 L mixing drum). The jacket temperature was set at 70° C. [Step 1]

In a next step, the citric acid is moistened over the course of about 3 minutes with about 20 mL water via the device's inlet port, while stirring at a speed of Fr 1.65-3.71 (about 100-150 rpm), preferably using the chopper blades of the device during at least the first minute to avoid the formation, or presence, of larger agglomerates in the mixture. [Step 2]

Subsequently, about 0.85 kg calcium carbonate ($CaCO_3$) is added to the same mixing chamber (about 2-3 wt.-% based on the citric acid), and granulated with the moistened citric acid for about 5 minutes at a temperature of about 65° C. C and while stirring at a speed of Fr 1.65-3.71 (about 100-150 rpm) in order to passivate the surface of the citric acid. [Step 3]

In the next step, about 3.40 kg potassium bicarbonate ($KHCO_3$) is added to the mixing chamber, and the mixture further granulated at a temperature of about 55° C., a stirring speed of Fr 1.05-3.71 (about 80-150 rpm), and using a vacuum that is cycling from $p_1$=450 mbar to $p_2$=850 mbar (due to the ongoing effervescent reaction in the evacuable mixing chamber) for about 3 minutes. This typically equals about 1-3 cycles. [Step 4]

Thereafter, the product is dried, in an initial 'stop'-drying step, at a temperature of about 55-65 C by stirring continuously at a stirring speed of about Fr 1.65 (about 100 rpm) until the pressure has reached about 60 mbar, before continuing the initial drying at a stirring speed of about Fr 0.81 (about 70 rpm) and using an interval stirring mode with 5 min off/0.25 min on, until the pressure is reduced to about 15 mbar or below. [Step 5]

After this initial 'stop'-drying step, the product is dried yet further, in a final 'stop'-drying step of about 15 min, at 15 mbar and a stirring speed of Fr 0.81 (about 70 rpm) and using an interval stirring mode with 5 min off/0.25 min on, with the heater being switched off. [Step 6]

Optionally, aroma, sweeteners, dyes, as well as other excipients commonly used for adjusting the organoleptic and/or handling properties of effervescent granules, can be added to thethus dried granular product. Upon such additions, the stirring speed should preferably not be increased beyond the stirring speed of the final 'stop'-drying step to make sure that excessive abrasion and/or comminution of the dried effervescent granules is avoided. [Step 7]

The process yielded K-containing effervescent granules with a bulk density in the range of from 0.98 g/mL to 1.00 g/mL, a Hausner ratio in the range of from 1.14 to 1.15, and a loss-on-drying (LOD, determined gravimetrically after 15 minutes at 70° C. and ambient pressure using a halogen moisture analyzer like HC103 by Mettler) in the range of from about 0.11 to about 0.15 wt.-%. The process yield was about 92-94 wt.-% based on the weights of the raw materials used. The effervescent granules of all tested lab-scale batches could be compressed into the target effervescent tablets with a weight of about 4.55 g, a hardness of about 90 N, and dissolution times of about 60 seconds in a glass of water (~250 mL).

Effervescent tablets (n=6) obtained from the effervescent granules of three different batches prepared according to the process of Example 2 were packaged and sealed in aluminium-lined sachets and stored at different temperatures for 7 days (55° C., 40° C. and 25° C.) to assess their storage stability. The three batches of effervescent granules differed in the stirrings speeds employed during preparation steps 2 to 4, as outlined in Table 3 below. Table 3 further lists how the respective effervescent tablets obtained from the effervescent granules of Batch 1 to 3 behaved with respect to storage stability in terms of i) gas formation within the sachet, as well as ii) the appearance of the effervescent tablets.

distinct gas formation in the sachets (i.e., the sachets were fully inflated and hardly compressible anymore upon light finger pressure). However, the tablets of the fast-stirred Batch 1 did not yet show any change in appearance, while the tablets of Batch 2 with the intermediate stirring speed were already exhibiting a 'glassy' appearance (i.e., the formerly white tablet surface appeared speckled with glass-shard like, translucent crystals), and the tablets of slow-stirred Batch 3 were already abreacted after 7 days at 55° C. (i.e., tablet lost their physical integrity due to efferscent reaction within the sachet). In that regard, it should be noted that this stability test condition (7 days at 55° C.) is a very hard challenge for effervescent tablets; regularly, a storage stability of 2 days at 55° C. is considered to be sufficient. In other words, the gas formation of the tablets of all three batches does not per se indicate a general storage instability issue. However, the differences observed in appearance changes at this challenging condition (batch 1 none, batch 2 glassy, batch 3 degraded) show that—surprisingly and very much in contrast with the hitherto understanding that effervescent granules should not be stirred fast during their preparation—the effervescent granules of the fastest-stirred batch (batch 1) actually yielded the most stable granules and respective tablets.

TABLE 3

Comparison of potassium-containing tablets obtained from three different effervescent granule batches (batches 1 and 2 prepared according to Example 2, batch 3 similarly but with deliberately slow stirring speeds <0.50 for comparison); Stirring speed and resulting storage stability

|  | Batch 1 | Batch 2 | Batch 3 |
| --- | --- | --- | --- |
| Stirring speed Step 2 | Fr 3.71 | Fr 1.65 | Fr 0.41 |
| Stirring speed Step 3 | Fr 3.71 | Fr 1.65 | Fr 0.41 |
| Stirring speed Step 4 | Fr 3.71 | Fr 1.05 | Fr 0.41 |
| Storage stability 7 days at 55° C. | Distinct gas formation observed Appearance: no change | Distinct gas formation observed Appearance: glassy | Distinct gas formation observed Appearance: degraded |
| Storage stability 7 days at 40° C. | No gas formation observed Appearance: no change | No gas formation observed Appearance: no change | Moderate gas formation observed Appearance: no change |
| Storage stability 7 days at 25° C. | No gas formation observed Appearance: no change | No gas formation observed Appearance: no change | No gas formation observed Appearance: no change |

As can be seen from Table 3, the inventors surprisingly found that it is in fact the faster-stirred batches that achieved the better stability, with e.g., Batch 1 that was stirred at Fr 3.71 throughout steps 2 to 4 (equaling ~150 rpm in the specific 20 L mixing drum used in Example 2) showing neither gas formation nor changes in appearance even when stored at 40° C. for 7 days. In contrast, with the slow-stirred Batch 3 (Fr 0.41; ~50 rpm) moderate gas formation was already observed at this storage condition (i.e., the sachets were slightly inflated, yet still easily compressible upon light finger pressure). The effervescent tablets obtained from the granules of Batch 2, which were stirred at intermediate speeds of Fr 1.05-165 (~80-100 rpm), also showed no gas formation or changes in appearance when stored at 40° C. for 7 days.

Upon raising the storage temperature from 40° C. to 55° C., the effervescent tablets of all three tested batches started showing signs of instability, as indicated, for instance, by a Example 3—Effervescent Granules as an Effervescent Base Composition/Labscale (Here ~7-8 kg)

Some drugs, such as acid-labile drugs or base-labile drugs, may be sensitive to being incorporated directly into effervescent granules, rather than being mixed with a granular effervescent base composition that is pre-formulated and dried. For the purpose of preparing such a granular effervescent base composition, about 1.9 kg citric acid was loaded into the evacuable mixing chamber of a ploughshare mixing device (here, a 20 L mixing drum of a Lödige laboratory mixing device; Gebrüder Lödige Maschinenbau GmbH; Germany), and heated under stirring to about 55-65° C. (e.g., about 64° C.) for about 9-20 min, with the stirring speed exhibiting a Froude number (Fr) of 2.78 (equals about 130 rpm for the dimensions of said 20 L mixing drum). The jacket temperature was set at 70° C.

In a next step, about 4.45 kg sodium bicarbonate (NaHCO$_3$) is added to the same mixing chamber and also heated at about 55-65° C. (e.g., about 60° C.) for a further 5-9 min and stirring at Fr 1.65 (about 100 rpm). To avoid a reaction starting during heating up, a vacuum of 15 mbar is applied periodically.

Subsequently, the mixture of citric acid and sodium bicarbonate is granulated by adding a first amount of about 5.6 mL of a saturated aqueous sodium citrate solution to the evacuable mixing chamber via the device's inlet port at a temperature of about 50-60 C, and using a vacuum that is cycling from $p_1$=150 mbar to $p_2$=450 mbar. During the first minute, when the solution is added, a high stirring speed of Fr 7.97 ($\approx$220 rpm) is chosen, and the chopper blades are preferably switched on to avoid the formation, or presence, of larger agglomerates in the mixture. For the remaining 3 minutes, the chopper blades, if used before, are switched off again, and the stirring speed reduced to about Fr 0.93-6.59 ($\approx$75-200 rpm).

Prior to the next step, the granulated product is dried once more, in a further intermediate 'stop'-drying step, at a temperature of about 55-65° C. (e.g., 64° C.) by stirring continuously at low stirring speeds of about Fr 0.93-1.33 ($\approx$75-90 rpm) for about 1 to 2 minutes before continuing drying under interval stirring (5 min off/0.25 min on) until the pressure has reached about 15 mbar or below.

Thereafter, the dried granules are granulated further by adding about 32 mL of an 28% ethanolic polyvinylpyrrolidone (PVP K25) solution to the evacuable mixing chamber via the device's inlet port at a temperature of about 60 C, and using a vacuum that is cycling from $p_1$=450 mbar to $p_2$=850 mbar. During the first 2 minutes, when the PVP-solution is added, a high stirring speed of Fr 7.97 ($\approx$220 rpm) is chosen, and the chopper blades are preferably switched on to avoid the formation, or presence, of larger agglomerates in the mixture. For the remaining 2 minutes, the chopper blades, if used before, are switched off again, and the stirring speed reduced to about Fr 0.93-3.71 ($\approx$75-150 rpm). At these stirring speeds, the tested batches ran through about 0.5-2 cycles.

Thereafter, about 0.14 kg sodium carbonate (Na$_2$CO$_3$) and about 0.95 kg mono sodium citrate were added to the moist granules in the mixing chamber, and the product dried, in an initial 'stop'-drying step, at a temperature of about 55-65° C. (e.g., 60, 62, or 63° C.) while stirring at slow speeds in the range of about Fr 0.93-1.82 ($\approx$75-105 rpm), gradually reducing the pressure to 15 mbar. Once reaching 100 mbar, the stirring speed during this 'stop'-drying step can optionally be reduced to about Fr 0.59-0.93 ($\approx$60-75 rpm); for instance, from Fr 1.82 to Fr 0.93 ($\approx$105 to 75 rpm), or from Fr 1.65 to 0.59 ($\approx$100 to 60 rpm) and interval stirring can be started (2 min off/0.25 min on).

After this initial 'stop'-drying step, the product is dried yet further, in a final 'stop'-drying step, with the heater being switched off and using reduced pressure as well as interval-stirring at very slow stirring speeds of about Fr 0.01 ($\approx$8 rpm; 2 min off/0.25 min on) for about 20 min.

The process yielded an effervescent base composition with granules of a bulk density in the range of from 0.87 g/mL to 0.93 g/mL, a Hausner ratio in the range of from 1.15 to 1.22, and a loss-on-drying (LOD, determined gravimetrically after 15 minutes) in the range of from about 0.21 to about 0.31 wt.-%, and a median particle size (DSO; as measured by dynamic image analysis, e.g., using a Camsizer® XT device) in the range of from about 110 µm to about 125 µm. The process yield was about 95.3-96 wt.-% based on the weights of the raw materials used.

As soon as they are cooled down to room temperature (20±5° C.), the granules of the effervescent base composition are ready to be mixed with drugs, including drugs that are sensitive to hydrolysis, oxidation, acids, bases (including carbonates), alkali-ions and/or earth-alkali ions. Optionally, aroma, sweeteners, dyes, as well as other excipients commonly used for adjusting the organoleptic and/or handling properties of effervescent granules (e.g., antifoaming agents, wetting agents, binders, etc), can be added to the dried granular product, too. As before, upon such additions, the stirring speed (or the mixing intensity, if blended in a device separate from the granulation device) should preferably not be increased beyond the stirring speed of the final 'stop'-drying step of the effervescent granules to make sure that excessive abrasion and/or comminution of the dried effervescent granules is avoided.

The final blends comprising the effervescent granules of all tested lab-scale batches could be compressed into the target effervescent tablets with a weight of about 2.23 g, a hardness of about 80 N, and dissolution times of about 65 seconds in a glass of water (— 250 mL).

Example 4—Effect of Stirring Speed

While the vast majority of prior art teaches away from using faster stirring speeds in the preparation of effervescent granules (such as stirring speeds exceeding Fr 0.50 during the effervescent reaction step), WO9421239A1 differs insofar as it describes stirring speeds as high as 250 rpm when preparing effervescent granules in a Zanchetta ROTO-50-P granulator (50 L mixing chamber), equating to a Froude-number of about 15, during at least parts of the effervescent reaction step.

Unfortunately, WO9421239A1 also teaches that the yields obtained at such high stirring speeds were found to be suboptimal; for instance 75-76% in Example 1 of WO9421239A1. Thus, in an attempt to evaluate the impact of stirring speeds further—and in particular to test whether choosing stirring speeds within the optimal Froude range as taught by the present invention and/or working with a horizontal mixing device helps to overcome the low-yield issues of WO9421239A1—the inventors ran a comparative test mimicking Example 1 of WO9421239A1 as outlined in Table 4 below. The left column of said table portrays the granulation process with stirring speeds chosen based on Example 1, the right column shows the same granulation process but using stirring speeds within the optimal Froude range as taught by the present invention, namely in the range of 0.50 to 8.00 during at least the effervescent reaction step (i.e., here the wetting step with the two liquid additions and the subsequent spreading of said liquid for further granulation before the first 'stop'-drying step).

The inventors followed Example 1 as closely as possible but—due to lack of access to a tiltable Zanchetta ROTO-50-P—used a horizontal ploughshare mixing device instead; namely, a 20 L Lödige laboratory mixing device. This required some minor adaptions to the granulation process of WO9421239A1. For instance, due to the smaller volume of the mixing chamber compared to the ROTO-50-P, smaller amounts of all components were used, such as 60 mL additions of deionized water instead of 150 mL, or using 8 kg of the citric acid and sodium bicarbonate blend (weight ratio of about 1.2:1) instead of 20 kg. Furthermore, stirring at Froude numbers of about 15 or 0.1 (i.e., the 250 rpm or 20 rpm used in the ROTO-50-P, respectively) is not possible with the Lödige laboratory mixing device; therefore, the inventors used the 280 rpm and 60 rpm stirring speeds possible with the Lödige device, instead. This translates to Froude numbers of 12.9 and 0.6, respectively, and is thus not too far removed from 15 and 0.1 used in WO9421239A1. Moreover, the Lödige device does not allow for tilting of the mixing chamber during the granulation process, but instead is positioned horizontally throughout. Thus, unlike suggested in Example 1 (which actually uses the high stirring speeds when in upright/vertical position, not while tilting back and forth between upright and horizontal orientation), both experiments of the present example were performed in a device with a horizontally oriented mixing chamber.

For the two experiments (the stirring conditions of which are summarised in Table 4 below), 4.56 kg citric acid and 3.84 kg sodium bicarbonate were first dry-blended without heating for 2 minutes in the evacuable 20 L mixing chamber of the Lödige mixing device with the chopper turned on. Subsequently, the dry-blend was moistened with a first 60 mL portion of deionized water being introduced into the mixing chamber via a top-spray nozzle. After 3 minutes, a second 60 mL portion of deionized water was added and the moistened blend allowed to react for another 5 minutes. Thereafter, the chopper was turned off, and stirring speed was reduced. After a further 6 minutes, heat was applied to the jacket of the vessel, and the vacuum was turned on. Once the product temperature reached 50° C., the chopper was turned back on, the stirring speed increased for the next 5 minutes, while the vacuum was turned off, in order to allow for accelerated heating of the product without the 'insulating' effects of the vacuum. Thereafter, the chopper was turned off, the vacuum turned back on, and the granules were stirred using interval stirring (6 min. off, 2 min. on), allowing the product temperature to reach 80° C. Then heating and vacuum was switched off and granules were allowed to cool down to at least 45° C. or lower before being emptied out from the mixing chamber.

As can be seen from Table 4 below, using stirring speeds within the optimal Froude range as taught by the present invention (namely in the range of 0.50 to 8.00 during at least the effervescent reaction step; see process 4B) led to significant improvements in both yield and process duration; 78% instead of 68% and only 175 minutes instead of 240 minutes. The granules from both processes could be compressed easily into effervescent tablets of target hardness (70-100 N), and showed a loss-on-drying value (determined gravimetrically after 15 minutes at 70° C. and ambient pressure using a halogen moisture analyzer like HC103 by Mettler) well below the preferred 0.50 wt.-%; namely, LOD 0.14% based on the initial weight prior to drying. This also led to good stability results for the effervescent tablets prepared from both granule batches when tested at accelerated storage conditions (here 50° C. for 2 days); i.e., no gas formation within the tablets' sachets and no changes in appearance of the tablets that were visible to the naked human eye.

Apart from increasing yield and shortening process time, process 4B with optimized stirring speeds according to the present invention also resulted in effervescent tablets with shorter dissolution times (70 sec vs. 130 sec) which is clearly beneficial from a user perspective.

However, as can also be seen from processes 4A and 4B in this example, when using the vacuum only during the drying steps as taught by WO9421239A1, while allowing the effervescent reaction—initiated by the moistening of the reactive components with a granuling liquid such as water—to occur at ambient pressure, the process is far less controlled and fails to provide more optimal yields such as 90% or higher.

TABLE 4

Comparison with prior art processes; impact of stirring speeds

|  | 4A - stirring speeds based on WO9421239A1 | 4B - stirring speeds in optimized range |
|---|---|---|
| Dry blending | Fr 12.9/Chopper: on<br>Preheating: no<br>2 min<br>Vacuum: off | Fr 3.7/Chopper: on<br>Preheating: no<br>2 min<br>Vacuum: off |
| Initiate effervescent reaction (moistening) | Fr 12.9/Chopper: on<br>add 60 mL/stir 3 min<br>add 60 mL/stir 5 min<br>Vacuum: off | Fr 3.7/Chopper: on<br>add 60 mL/stir 3 min<br>add 60 mL/stir 5 min<br>Vacuum: off |
| Continued effervescent reaction | Fr 0.6/Chopper: off<br>stir 6 min<br>Vacuum: off | Fr 3.7/Chopper: off<br>stir 6 min<br>Vacuum: off |
| Initial 'stop'-drying step | Fr 0.6/Chopper: off<br>Product-temp.: up to 50° C.<br>Vacuum: on | Fr 0.6/Chopper: off<br>Product-temp.: up to 50° C.<br>Vacuum: on |
| Accelerated heating | Fr 12.9/Chopper: on<br>5 min<br>Vacuum: off | Fr 3.7/Chopper: on<br>5 min<br>Vacuum: off |
| Final 'stop'-drying step | Fr 0.6 interval (6 min off/<br>2 min on)/Chopper: off<br>Product-temp.: up to 80° C.<br>Vacuum: on | Fr 0.6 interval (6 min off/<br>2 min on)/Chopper: off<br>Product-temp.: up to 80° C.<br>Vacuum: on |
| Cool down | Fr 0.6 interval (6 min off/<br>2 min on)/Chopper: off<br>Product-temp.: ≤45° C.<br>Vacuum: off | Fr 0.6 interval (6 min off/<br>2 min on)/Chopper: off<br>Product-temp.: ≤45° C.<br>Vacuum: off |

TABLE 4-continued

Comparison with prior art processes; impact of stirring speeds

| | 4A - stirring speeds based on WO9421239A1 | 4B - stirring speeds in optimized range |
|---|---|---|
| Process duration | 240 min | 175 min |
| Yield | 68% | 78% |
| Loss-on-drying (15 min at 70° C.) | 0.14% | 0.14% |
| Bulk density (poured) | 0.77 g/mL | 0.89 g/mL |
| Tabletting behaviour | very good | very good |
| Dissolution time | 130 sec | 70 sec |
| Stability (2 d at 55° C.) | good | good |

The following list of numbered items are embodiments comprised by the present invention:

1. A method for the preparation of effervescent granules, wherein at least one acidic effervescent component and at least one alkaline $CO_2$-generating effervescent component as the reactive components are brought to reaction with one another under stirring in a vacuum in an evacuable mixing chamber, wherein, after loading at least the reactive components, the mixing chamber is evacuated to a first vacuum value $p_1$, and wherein the mixing chamber is evacuated to said first vacuum value $p_1$ again, optionally repeatedly, once the pressure has increased to a second vacuum value $p_2$ as a result of the progressing $CO_2$-formation of the effervescent reaction in the mixing chamber, and wherein the effervescent reaction is carried out in a vacuum range $p_1$ to $p_2$ of 100 to 900 mbar, and
   wherein the effervescent reaction is stopped by drying the effervescent granules under vacuum in a 'stop'-drying step,
   wherein during at least the effervescent reaction step(s) the stirring speed in the mixing chamber exhibits a Froude number (Fr) in the range of 0.50 to 8.00, preferably in the range of 0.80 to 8.00, more preferably in the range of 0.90 to 8.00.
2. The method according to item 1, wherein the evacuable mixing chamber is oriented horizontally.
3. The method according to items 1 or 2, wherein during the 'stop'-drying step(s) the stirring speed in the mixing chamber exhibits a Froude number (Fr) of 0.25 or higher.
4. The method according to any one of the preceding items, wherein during the 'stop'-drying step(s) the stirring speed in the mixing chamber exhibits a Froude number (Fr) of 0.25 to 5.00
5. The method according to any one of the preceding items, wherein during at least the effervescent reaction step(s) the stirring speed in the mixing chamber is higher than during the 'stop'-drying step(s).
6. The method according to any one of the preceding items, wherein the effervescent reaction is carried out in a vacuum range $p_1$ to $p_2$ of 150 to 850 mbar.
7. The method according to any one of the preceding items, wherein the difference between $p_1$ and $p_2$, at least during the effervescent reaction step, is in the range of from 200 to 500 mbar, or from 250 to 450 mbar, or from 300 to 400 mbar.
8. The method according to any one of the preceding items, wherein the at least one acidic effervescent component is an organic acid or a mixture of organic acids, preferably an organic acid selected from the group consisting of citric acid, tartaric acid, malic acid, fumaric acid, adipic acid, or a mixture thereof; and/or wherein the at least one alkaline $CO_2$-generating effervescent component selected from the group consisting of hydrogen carbonates and carbonates of alkaline metals and alkaline earth metals, or a mixture thereof, preferably selected from the group consisting of sodium hydrogen carbonate, sodium carbonate, potassium hydrogen carbonate, potassium carbonate, magnesium carbonate, and calcium carbonate, or a mixture thereof
9. The method according to any one of the preceding items, wherein the first effervescent reaction step is preceded by a prewarming step for bringing at least one, optionally all, of the reactive components to a target product temperature prior to reacting them with one another.
10. The method according to item 9, wherein the stirring speed in the mixing chamber exhibits a Froude number (Fr) in the range of 0.50 to 8.00 during the prewarming step and the effervescent reaction step, preferably in the range of 0.80 to 8.00, more preferably in the range of 0.90 to 8.00.
11. The method according to items 9 to 10, wherein the at least one acidic effervescent component comprises, or consists of, citric acid, and wherein at least the citric acid is brought to a target product temperature (e.g., 55-70° C., or 55-65° C.) prior to reacting it with the at least one alkaline $CO_2$-generating effervescent component.
12. The method according to any one of the preceding items, wherein the effervescent reaction is initiated by addition of a granulating liquid, optionally an aqueous, alcoholic or hydroalcoholic granulating liquid.
13. The method according to item 12, wherein the granulating liquid is added in two or more fractions thereof, with an intermediate 'stop'-drying step in between the additions of the two or more fractions.
14. The method according to item 12 to 13, wherein the granulating liquid is introduced into the evacuable mixing chamber via at least one top-spray nozzle.
15. The method according to any one of the preceding items, wherein the effervescent granules obtained in the 'stop'-drying step, more specifically the last 'stop'-drying step, are processed further in the same evacuable mixing chamber, and wherein the stirring speed in the mixing chamber exhibits a Froude number (Fr) of 0.25 or higher during this at least one further processing step.

16. The method according to item 15, wherein the mixing speed is in the range of Fr 0.25 to 4.30, or 0.25 to 3.80, or 0.25 to 2.00, or 0.25 to 1.60, or 0.25 to 1.10 during the further processing step.
17. The method according to items 15 or 16, wherein the effervescent granules obtained in the 'stop'-drying step, more specifically the last 'stop'-drying step, are processed further in the same evacuable mixing chamber by mixing them with one or more additional components selected from pharmaceutically or nutraceutically acceptable active ingredients and/or pharmaceutically or nutraceutically acceptable excipients.
18. The method according to any one of the preceding items, wherein the effervescent granules a loss-on-drying of ≤1.50 wt.-%, based on the initial weight prior to drying, preferably ≤1.00 wt.-%, more preferably ≤0.75 wt.-%, and further preferably ≤0.50 wt.-%, as determined gravimetrically after 15 minutes at 70° C. and ambient pressure.
19. The method according to any one of the preceding items, wherein the effervescent granules exhibit a Hausner ratio (i.e., tapped bulk density divided by freely settled bulk density) in the range of 1.10 to 1.40, or 1.15 to 1.30.
20. The method according to any one of the preceding items, wherein the effervescent granules are storage stable.
21. The method according to any one of the preceding items, wherein the effervescent granules, when compressed into effervescent tablets of a hardness in the range of to 120 N, exhibit dissolution times in water at room temperature (20±5° C.) of ≤150 seconds, preferably ≤120 seconds, more preferably ≤90 seconds, and further preferably ≤60 seconds.
22. Effervescent granules obtained by the method according to items 1 to 21.

The invention claimed is:

1. A method for the preparation of effervescent granules, wherein at least one acidic effervescent component and at least one alkaline $CO_2$-generating effervescent component as the reactive components are brought to reaction with one another under stirring in a vacuum in an evacuable mixing chamber to form the effervescent granules, wherein, after loading at least the reactive components, the mixing chamber is evacuated to a first vacuum value $p_1$, and wherein the mixing chamber is evacuated to said first vacuum value $p_1$ again, optionally repeatedly, once the pressure has increased to a second vacuum value $p_2$ as a result of a progressing $CO_2$-formation of an effervescent reaction in the mixing chamber, and
wherein the effervescent reaction is carried out in a vacuum range $p_1$ to $p_2$ of 100 to 900 mbar, and wherein the effervescent reaction is stopped by drying the effervescent granules under vacuum in a 'stop'-drying step, wherein during at least the effervescent reaction step(s) a stirring speed in the mixing chamber exhibits a Froude number (Fr) in the range of 0.50 to 8.00.
2. The method according to claim 1, wherein the evacuable mixing chamber is oriented horizontally.
3. The method according to claim 1, wherein during the 'stop'-drying step(s) the stirring speed in the mixing chamber exhibits a Froude number (Fr) of 0.25 or higher.
4. The method according to claim 1, wherein during at least the effervescent reaction step(s) the stirring speed in the mixing chamber is higher than during the 'stop'-drying step(s).
5. The method according to claim 1, wherein the effervescent reaction is carried out in a vacuum range $p_1$ to $p_2$ of 150 to 850 mbar.
6. The method according to claim 1, wherein the difference between $p_1$ and $p_2$, at least during the effervescent reaction step, is in the range of from 200 to 500 mbar, or from 250 to 450 mbar, or from 300 to 400 mbar.
7. The method according to claim 1, wherein the at least one acidic effervescent component is an organic acid or a mixture of organic acids, and/or wherein the at least one alkaline $CO_2$-generating effervescent component is selected from the group consisting of hydrogen carbonates and carbonates of alkaline metals and alkaline earth metals, and mixtures thereof.
8. The method according to claim 1, wherein the first effervescent reaction step is preceded by a prewarming step for bringing at least one, optionally all, of the reactive components to a target product temperature prior to reacting them with one another.
9. The method according to claim 8, wherein the stirring speed in the mixing chamber exhibits a Froude number (Fr) in the range of 0.50 to 8.00 during the prewarming step and the effervescent reaction step.
10. The method according to claim 1, wherein the effervescent reaction is initiated by addition of a granulating liquid, optionally an aqueous, alcoholic or hydroalcoholic granulating liquid.
11. The method according to claim 10, wherein the granulating liquid is added in two or more fractions thereof, with an intermediate 'stop'-drying step in between the additions of the two or more fractions.
12. The method according to claim 10, wherein the granulating liquid is introduced into the evacuable mixing chamber via at least one top-spray nozzle.
13. The method according to claim 1, wherein the effervescent granules obtained in the last 'stop'-drying step, are processed further in at least one further processing step in the same evacuable mixing chamber, and wherein the stirring speed in the mixing chamber exhibits a Froude number (Fr) of 0.25 or higher during this at least one further processing step.
14. The method according to claim 13, wherein the stirring speed is in the range of Fr 0.25 to 4.30, or 0.25 to 3.80, or 0.25 to 2.00, or 0.25 to 1.60, or 0.25 to 1.10 during the at least one further processing step.
15. The method according to claim 1, wherein during at least the effervescent reaction step(s) the stirring speed in the mixing chamber exhibits a Froude number (Fr) in the range of 0.80 to 8.00.
16. The method according to claim 1, wherein during at least the effervescent reaction step(s) the stirring speed in the mixing chamber exhibits a Froude number (Fr) in the range of 0.90 to 8.00.
17. The method according to claim 7, wherein the at least one acidic effervescent component is an organic acid, or a mixture of organic acids, selected from the group consisting of citric acid, tartaric acid, malic acid, fumaric acid, adipic acid, or and a mixture thereof.
18. The method according to claim 7, wherein the at least one alkaline $CO_2$-generating effervescent component is selected from the group consisting of sodium hydrogen carbonate, sodium carbonate, potassium hydrogen carbonate, potassium carbonate, magnesium carbonate, and calcium carbonate, of and a mixture thereof.
19. The method according to claim 9, wherein the stirring speed in the mixing chamber exhibits a Froude number (Fr)

in the range of 0.80 to 8.00 during the prewarming step and the effervescent reaction step.

20. The method according to claim 9, wherein the stirring speed in the mixing chamber exhibits a Froude number (Fr) in the range of 0.90 to 8.00 during the prewarming step and the effervescent reaction step.

* * * * *